United States Patent
Tegg

(10) Patent No.: US 7,823,258 B2
(45) Date of Patent: Nov. 2, 2010

(54) SELF-LOCKING WIRE LOCK

(75) Inventor: Troy T. Tegg, Elk River, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 698 days.

(21) Appl. No.: 11/647,349

(22) Filed: Dec. 29, 2006

(65) Prior Publication Data

US 2008/0159825 A1 Jul. 3, 2008

(51) Int. Cl.
*F16B 37/12* (2006.01)
(52) U.S. Cl. .................. 24/136 R; 24/115 M
(58) Field of Classification Search ............. 24/136 R, 24/115 M, 25
See application file for complete search history.

(56) References Cited

U.S. PATENT DOCUMENTS

| | | | | |
|---|---|---|---|---|
| 130,032 | A * | 7/1872 | Fautz | 24/25 |
| 199,788 | A * | 1/1878 | Chapman | 24/25 |
| 296,686 | A * | 4/1884 | Gresham | 24/25 |
| 1,712,566 | A * | 5/1929 | Kraemer | 24/194 |
| 1,794,458 | A * | 3/1931 | Herschede | 24/194 |
| 2,491,290 | A * | 12/1949 | Tinnerman | 24/16 R |
| 2,503,793 | A * | 4/1950 | Breemes | 43/44.87 |
| 2,611,211 | A * | 9/1952 | Stockton | 43/44.91 |
| 3,976,079 | A * | 8/1976 | Samuels et al. | 24/115 M |
| 4,208,770 | A * | 6/1980 | Takada | 24/136 K |
| 5,395,329 | A | 3/1995 | Fleischhacker et al. | |
| 5,861,024 | A | 1/1999 | Rashidi | |
| 6,308,090 | B1 | 10/2001 | Tu et al. | |
| 6,511,100 | B1 * | 1/2003 | Le Clinche | 285/316 |
| 7,143,481 | B2 * | 12/2006 | Komai et al. | 24/20 R |
| 2003/0074019 | A1 | 4/2003 | Gray et al. | |
| 2003/0115723 | A1 * | 6/2003 | Shuey | 24/136 R |
| 2004/0144827 | A1 | 7/2004 | Fox | |
| 2005/0155189 | A1 * | 7/2005 | Komai et al. | 24/19 |
| 2005/0165406 | A1 | 7/2005 | Assell et al. | |

OTHER PUBLICATIONS

International Search for PCT/US07/89132 filed Dec. 28, 2007 with International Search Report and Written Opinion dated Jun. 11, 2008.

* cited by examiner

*Primary Examiner*—Robert J Sandy
(74) *Attorney, Agent, or Firm*—Wiley Rein LLP

(57) ABSTRACT

A wire lock includes a body having an opening therethrough, a locking member disposed at least partially within the opening, and a biasing device. The biasing device urges the locking member into a configuration wherein a wire passing through the opening is restrained in at least one direction, and may operate in either tension or compression. The locking member may include one or more locking elements that are compressed about the wire through engagement with a wedge-shaped locking section of the body, with the biasing member urging the locking member against the locking section. In other embodiments, the locking member is a locking pin riding on an inclined surface of an elongate slot extending across the body, with the biasing member urging the locking pin against one end of the slot, and the wire pinched between the pin and a body surface opposite the inclined surface.

18 Claims, 6 Drawing Sheets

SELF-LOCKING WIRE LOCK

BACKGROUND OF THE INVENTION a. Field of the Invention

The instant invention relates to steerable catheters. In particular, the instant invention relates to a self-locking wire lock for use in coupling steering wires to steerable catheter actuators.

b. Background Art

Catheters are used for an ever growing number of procedures. To name just a few examples, catheters are used for diagnostic, therapeutic, and ablative procedures. Typically, the physician manipulates the catheter through the patient's vasculature to the intended site, such as a site within the patient's heart. The catheter typically carries one or more electrodes or other diagnostic or therapeutic devices, which may be used for ablation, diagnosis, or the like.

It is well known that, to facilitate manipulation of the catheter through the patient's vasculature to the intended site, portions of the catheter shaft, especially the distal regions thereof, may be made steerable. That is, the catheter may be manufactured such that the physician can deflect the distal end of the catheter as necessary and desired to negotiate the tortuous paths of the patient's vasculature en route to the target site. Often, steerability is achieved by installing one or more steering wires (sometimes referred to as "pull wires") along the length of the catheter shaft. These steering wires are coupled to one or more actuators that the physician can utilize to selectively tension the wires, thereby deflecting the distal end of the catheter. An example of such a steerable catheter is disclosed and taught in U.S. Pat. No. 5,861,024 to Rashidi, the contents of which are incorporated herein by reference. Other steerable catheters are disclosed in U.S. Pat. Nos. 5,395,329 and 6,308,090, both of which are hereby incorporated by reference as though fully set forth herein.

A number of methods and devices exist for coupling the steering wires to the actuators. In some steerable catheters, the end of the wire is wrapped about a screw and frictionally held in place between the screw head and the actuator when the screw is tightened down. In other devices, the wire is first placed over a hole in the actuator, and a set device, such as a pin or set screw, is then placed into the hole such that the wire is pinched between the set device and the wall defining the hole. Alternatively, the wire may simply be tied to a feature on the actuator. Such methods, however, are cumbersome, especially if subsequent adjustments to the wire are necessary.

BRIEF SUMMARY OF THE INVENTION

Disclosed herein is a self-locking wire lock that facilitates the simple attachment and adjustment of a catheter steering wire to the actuator. The wire lock generally includes a body having an opening extending therethrough, a locking member disposed at least partially within the opening, and a biasing device. The biasing device urges the locking member into a locked configuration wherein a wire passing through the opening is restrained in at least one direction.

According to a first embodiment of the present invention, the wire lock includes a body having an opening extending axially therethrough, the opening being defined by an interior surface of the body and including a wedge-shaped locking section adjacent an end thereof; a locking assembly located at least partially within the opening and including a plurality of locking balls; and a spring located within the opening and biasing the locking assembly against the wedge-shaped locking section. With the locking assembly biased against the locking section, a wire passing through the opening is restrained in at least one axial direction. A hollow set device secures the spring and the locking assembly within the opening. Optionally, the hollow set device and the body include mating threads. The locking balls may be disposed at least partially within a carriage. Preferably, there are three substantially co-planar locking balls within the locking assembly. The wedge-shaped locking section has a preferred wedge angle between about 5 degrees and about 15 degrees, more preferably between about 10 degrees and about 15 degrees, and most preferably about 12 degrees, and may be a frusto-conical locking section. A release segment of the locking assembly may extend out of the opening.

In another embodiment of the invention, the wire lock includes a body having an opening defined by an interior surface of the body extending therethrough and including a locking section adjacent an end thereof; a locking assembly located at least partially within the opening; and a spring located within the opening and biasing the locking assembly against the locking section. The locking assembly permits a wire passing therethrough to move freely in a first direction and prevents the wire from moving in a second, opposite direction. The locking section exerts a compressive force on the locking assembly. For example, the locking section may include a wedge-shaped section that compresses the locking assembly when the spring forces the locking assembly against the wedge-shaped section. The locking assembly includes a carriage and at least one locking element at least partially disposed within the carriage. The at least one locking element may be three substantially co-planar locking balls.

In a further embodiment of the invention, the wire lock includes a body having an opening extending therethrough, the opening being defined by an interior surface of the body and including a wedge-shaped locking section; a locking assembly located at least partially within the opening; and a device located within the opening and biasing the locking assembly against the locking section such that a wire passing through the opening is permitted to move freely in one direction and prevented from moving freely in the opposite direction. The locking section may be located adjacent an end of the interior surface. The biasing device may be either a compression element that pushes the locking assembly against the locking section or a tension element that pulls the locking assembly against the locking section. In either case, a spring may be utilized.

According to yet another embodiment of the present invention, the wire lock includes a body having an opening extending axially therethrough; a slot extending across the body and intersecting the opening at substantially a right angle; a locking pin disposed within the slot; and a spring biasing the locking pin towards the proximal end of the slot. The proximal end of the slot is narrower than the distal end of the slot, such that, with the locking pin biased towards the proximal end of the slot, a wire passing through the opening is restrained in at least one axial direction. The slot may be an elongate slot defined by an axial surface, an inclined surface opposite the axial surface, a distal end surface, and a proximal end surface. The distal and proximal end surfaces join the axial and inclined surfaces. The locking pin rides on the inclined surface, and the wire passes and is pinched between the locking pin and a surface of the body opposite the inclined surface. Relative to the longitudinal axis of the body, the angle of the inclined surface is preferably between about 5 degrees and about 15 degrees, more preferably between about 5 degrees and about 10 degrees, and most preferably about 7 degrees.

In still a further embodiment of the present invention, the wire lock includes a body having an opening extending therethrough; a slot extending across the body and intersecting the opening at substantially a right angle; and a locking pin disposed within the slot. The locking pin permits a wire passing through the opening to move freely in one first direction and prevents the wire from moving in the opposite direction. To this end, the locking pin rides on a first surface partially defining the slot and entraps the wire against a body surface opposite the first surface. The wire lock optionally includes a biasing device configured to apply pressure between the locking pin and a wire passing through the body.

In yet another embodiment of the present invention, the wire lock includes a body having an opening extending therethrough; a slot extending across the body and intersecting the opening at substantially a right angle, the slot having a narrow end and a wide end; a locking pin disposed within the slot; and a device biasing the locking pin against the narrow end of the slot. The biasing device may be either a compression member that pushes the locking pin against the narrow end of the slot or a tension member that pulls the locking pin against the narrow end of the slot. In either case, the biasing device may be a spring.

In still another aspect of the present invention, a method of manufacturing a wire lock for use with a wire includes the steps of: providing a body having an opening extending therethrough and including a locking section; installing at least one locking element at least partially within the opening; and biasing the at least one locking element into a locked configuration against the locking section, whereby, upon inserting a wire into the opening, the wire is restrained in at least one axial direction via a compressive force exerted on the wire by the at least one locking element. Typically, the locking section will include an inclined surface along which the at least one locking element rides, and the inclined surface will be oriented such that the compressive force exerted on the wire increases as the wire is axially moved in the direction in which it is restrained. The compressive force may be made to decrease, thereby permitting insertion or removal of the wire, by urging the at least one locking element in the axial direction opposite the axial direction in which the wire is restrained.

An advantage of the present invention is that coupling the steering wire to the actuator is simplified.

Another advantage of the present invention is that subsequent adjustments to the steering wire are simplified.

Still another advantage of the present invention is that the biasing device's restorative force acts to lock the wire lock, resulting in a self-locking device.

Yet another advantage of the present invention is that it provides improved resistance to any potential de-coupling of the steering wire from the actuator.

The foregoing and other aspects, features, details, utilities, and advantages of the present invention will be apparent from reading the following description and claims, and from reviewing the accompanying drawings.

DETAILED DESCRIPTION OF THE INVENTION

Figure 1:
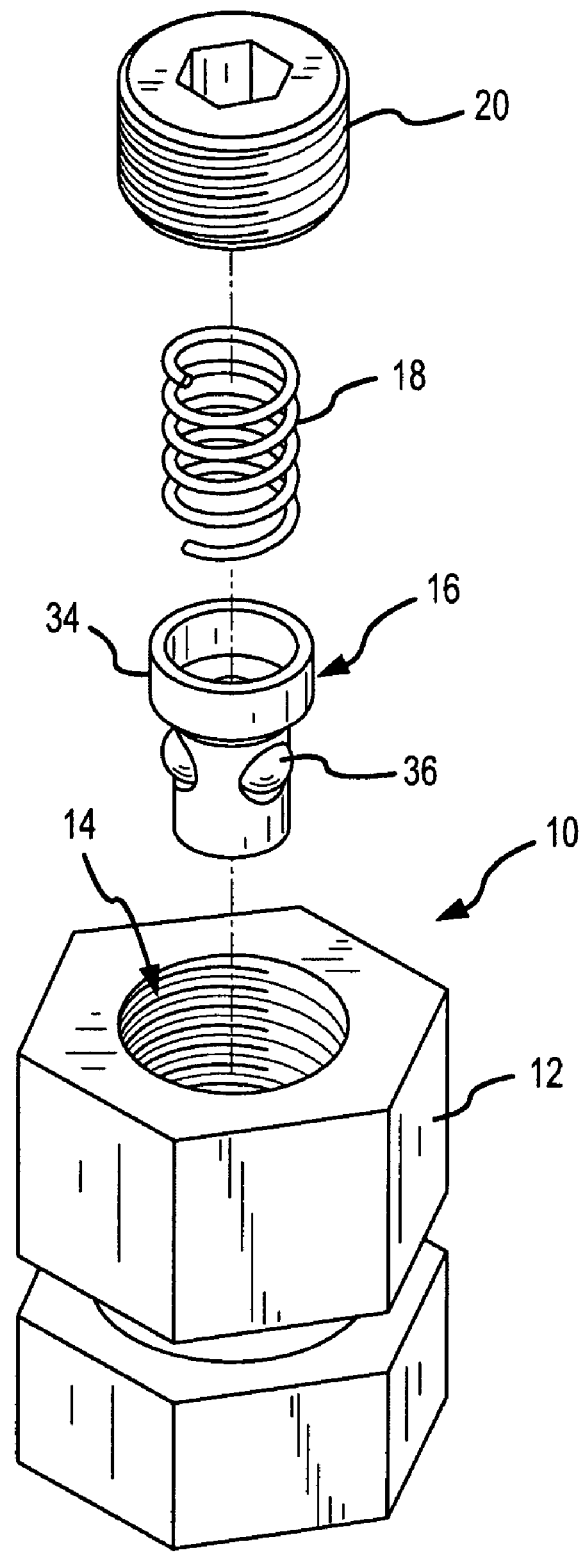
FIG. 1 is an exploded view of a wire lock according to a first embodiment of the invention.

FIG. 1 illustrates, in exploded view, a wire lock 10 according to a first embodiment of the invention. Wire lock 10 generally includes a body 12 having an opening 14 extending axially therethrough, a locking assembly 16 disposed at least partially within opening 14, and a biasing device 18, such as a coil spring, disposed within opening 14. A hollow set device 20, for example a set screw, may secure locking assembly 16 and biasing device 18 within opening 14, for example through the use of mating internal and external threads on body 12 and hollow set device 20, respectively. Other methods of affixing hollow set device 20 to body 12, including, but not limited to, frictionally fitting, tack welding, or fusing hollow set device 20 to body 12, are also contemplated.

Figure 2:
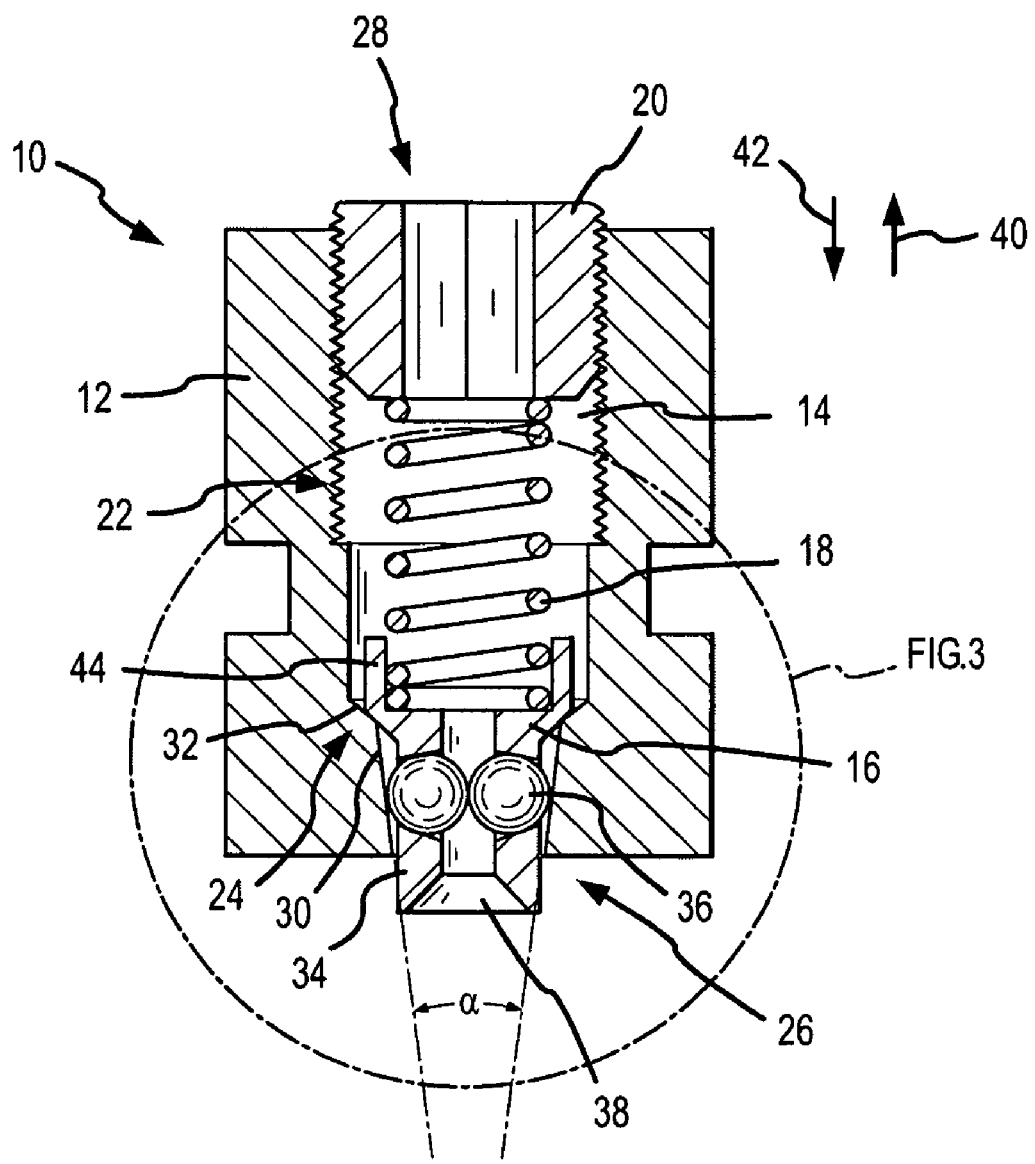
FIG. 2 depicts the wire lock of FIG. 1 in axial cross-section.
Figure 4:
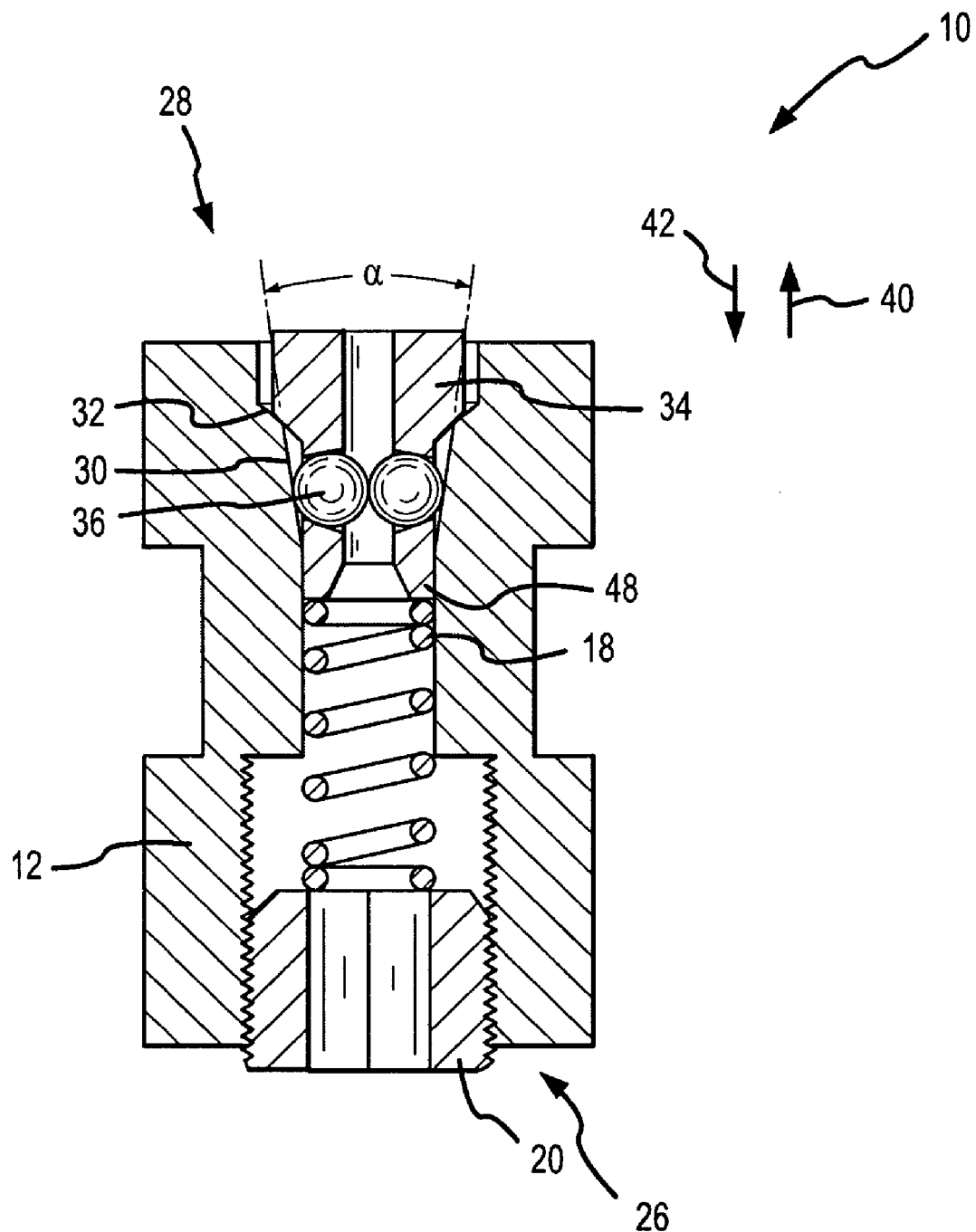
FIG. 4 is an axial cross-sectional view of a round wire lock utilizing a tension member biasing device according to a variation of the first embodiment of the invention.

As shown in FIG. 2, opening 14 is defined by an interior surface 22 of body 12. Interior surface 22 includes a locking section 24 configured to exert a compressive force on locking assembly 16. In the embodiment illustrated in FIGS. 1 and 2, locking section 24 is located adjacent a wire-entry end 26 of body 12, though it should be understood that body 12 may also be configured such that locking section 24 is located elsewhere along interior surface 22 without departing from the scope of the present invention. For example, locking section 24 may be located adjacent wire-exit end 28, as illustrated in FIG. 4, or substantially centrally located between wire-entry and wire-exit ends 26, 28. These latter configurations are described in further detail below.

Locking section 24 includes a wedge-shaped section 30 configured to compress locking assembly 16. Wedge-shaped section 30 is preferably a substantially continuous frustoconical section, though the use of one or more discrete wedge-shaped sections in locking section 24 is contemplated. Locking section 24 further includes a shoulder section 32 on which locking assembly 16 rides. A wedge angle α, which facilitates the compression of locking assembly 16 as locking assembly 16 rides on shoulder section 32 in contact with wedge-shaped section 30, is preferably between about 5 degrees and about 15 degrees, more preferably between about 10 degrees and about 15 degrees, and most preferably about 12 degrees. It will be apparent to one of skill in the art from this disclosure that adjusting wedge angle α will alter the compressive force exerted by locking section 24 on locking assembly 16.

Locking assembly 16 includes a carriage 34 and at least one locking element 36 disposed at least partially within carriage 34. A release segment 38 extends out of opening 14. Preferably, carriage 34 includes a plurality of locking balls, and most preferably includes three co-planar locking balls at 120 degree intervals. An interstitial space is defined between the co-planar locking balls through which a wire may pass. The locking balls may be made of a rigid plastic or composite, stainless steel, or tungsten carbide, though they are preferably made of chromium steel.

Figure 3:
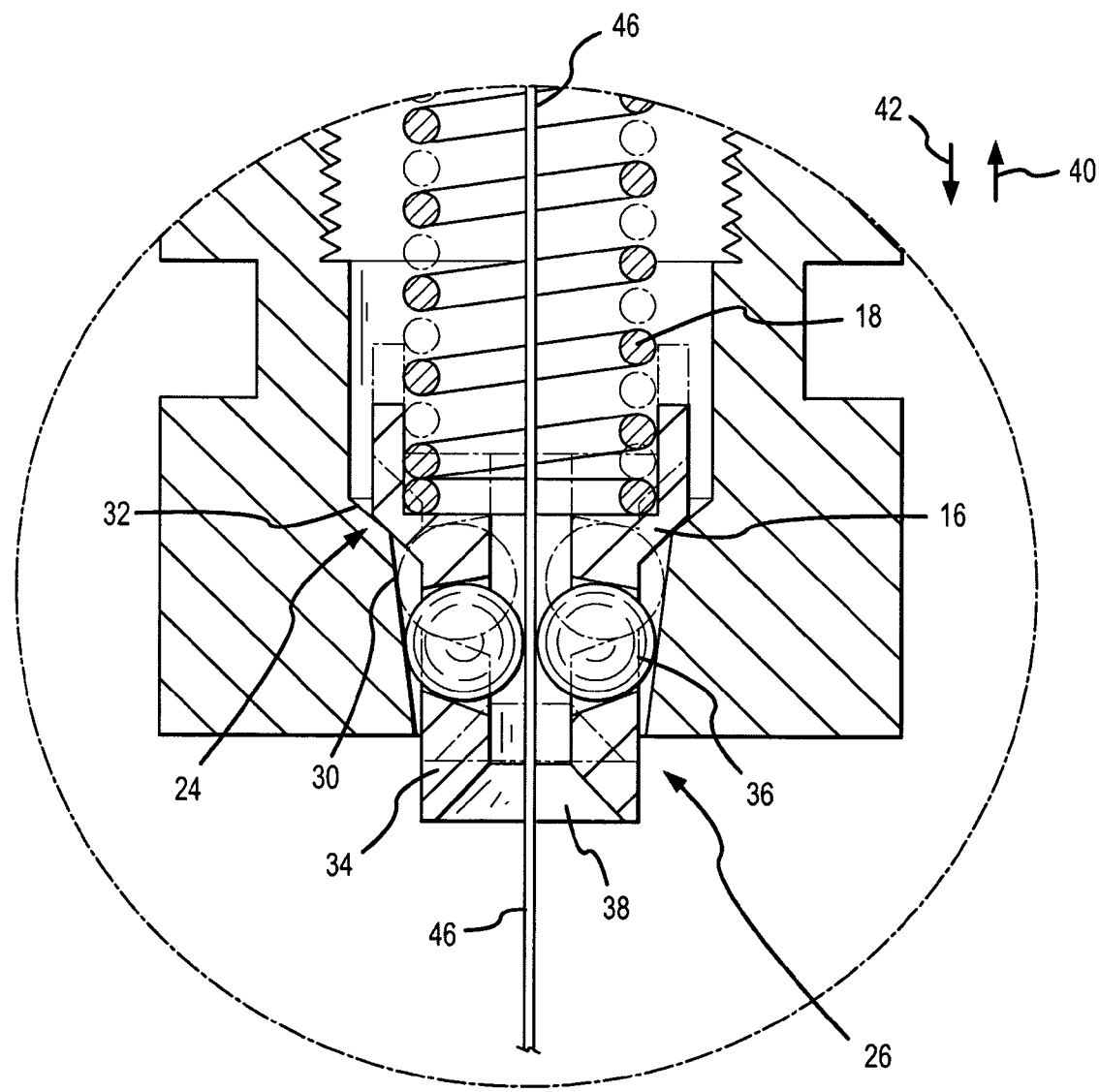
FIG. 3 is a close up view of the locking section of the wire lock illustrated in FIG. 2.

Biasing device 18 biases locking assembly 16 against locking section 24 in order to restrain, in at least one axial direction, a wire passing through opening 14. For example, as shown in FIGS. 2 and 3, a wire passing through locking assembly 16 moves freely in a first direction indicated by arrow 40, but is prevented from moving in a second, opposite direction indicated by arrow 42. In the embodiment of wire lock 10 illustrated in FIGS. 1-3, biasing device 18 is a compression member having its ends secured between locking assembly 16 and hollow set device 20. As illustrated, biasing device 18 is seated against an upper portion 44 of carriage 34 such that the restorative force of biasing device 18 pushes locking assembly 16 into contact with locking section 24. It is also contemplated that the ends of biasing device 18 may be attached either to upper portion 44 of carriage 34, to hollow set device 20, or to both upper portion 44 of carriage 34 and hollow set device 20. It should be understood, however, that attachment is not necessary when biasing device 18 is a compression member.

The operation of wire lock 10 will be described with reference to FIG. 3, which is an enlarged view of locking assembly 16, biasing device 18, and locking section 24. A round wire 46 is loaded into opening 14 of wire lock 10 from wire-entry end 26 in the direction of arrow 40 such that it passes through locking assembly 16, in particular through the interstitial space defined between locking elements (i.e., locking balls) 36. As shown in phantom in FIG. 3, as wire 46 is loaded, locking assembly 16 is urged upwards, away from locking section 24, by pushing upwards on release segment 38, thereby compressing biasing device 18. As locking assembly 16 is urged upwards, and thus towards wider regions of wedge shaped section 30, the compressive force exerted on carriage 34 by wedge shaped section 30 is reduced. This, in turn, permits separation between locking elements 36, thereby facilitating free movement of wire 46 in the direction of arrow 40.

Once release segment 38 is no longer being pushed upward, however, biasing device 18 re-expands, its restorative force urging locking assembly 16 back into contact with locking section 24. This, in turn, increases the compressive force exerted on carriage 34 by wedge shaped section 30 and forces locking elements 36 together, securing wire 46 between locking elements 36 using compressive forces. Wire lock 10 is thus self-locking. Further, if one attempts to pull wire 46 in the direction of arrow 42 in an effort to remove it from wire lock 10, the compressive force exerted on carriage 34 will increase as locking assembly 16 is forced into still narrower regions of wedge shaped section 30, thereby increasing the locking force exerted on wire 46 and substantially preventing movement of wire 46 in the direction of arrow 42. If one wishes to remove wire 46 from wire lock 10, one pushes release segment 38 upwards (i.e., in the direction of arrow 40), thereby permitting separation between locking elements 36 as described above, while simultaneously pulling wire 46 in the direction of arrow 42.

As described above, locking section 24 need not be located adjacent wire-entry end 26 as illustrated in FIGS. 1-3. It is also contemplated that locking section 24 may be located adjacent wire-exit end 28 as shown in FIG. 4. In this instance, biasing device 18 is a tension member that is attached at one end to the lower portion 48 of carriage 34 and at its other end to hollow set device 20 such that biasing device 18 pulls locking assembly 16 into contact with locking section 24. The interaction between locking assembly 16 and locking section 24 and the operation of this embodiment of wire lock 10 is substantially as described above with reference to FIG. 3, with the principal difference being that, as wire 46 is loaded, biasing device 18 is placed in tension rather than compression, for example by utilizing a tool to pull upwardly on locking assembly 16 in the direction of arrow 40.

Additionally, as further described above, locking section 24 may be located between wire-entry and wire-exit ends 26, 28. One skilled in the art should recognize from this disclosure that, when locking section 24 is located between wire-entry and wire-exit ends 26, 28, the components of wire lock 10 may be arranged in either configuration described above. That is, biasing device 18 may be either a compression member, as described with reference to FIG. 3, or a tension member, as described with reference to FIG. 4. Alternatively, dual biasing devices 18—both a tension member and a compression member—may be utilized.

Figure 5:
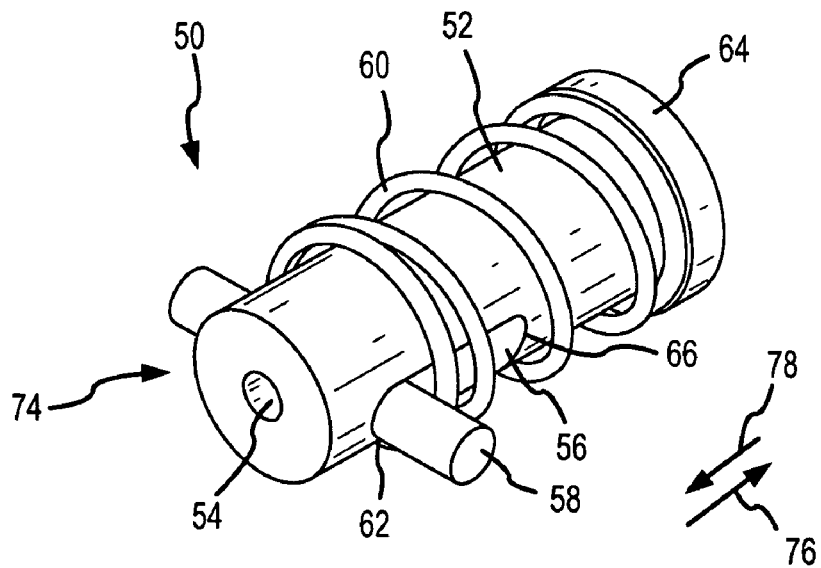
FIG. 5 is a perspective view of a wire lock according to another embodiment of the present invention.
Figure 6:
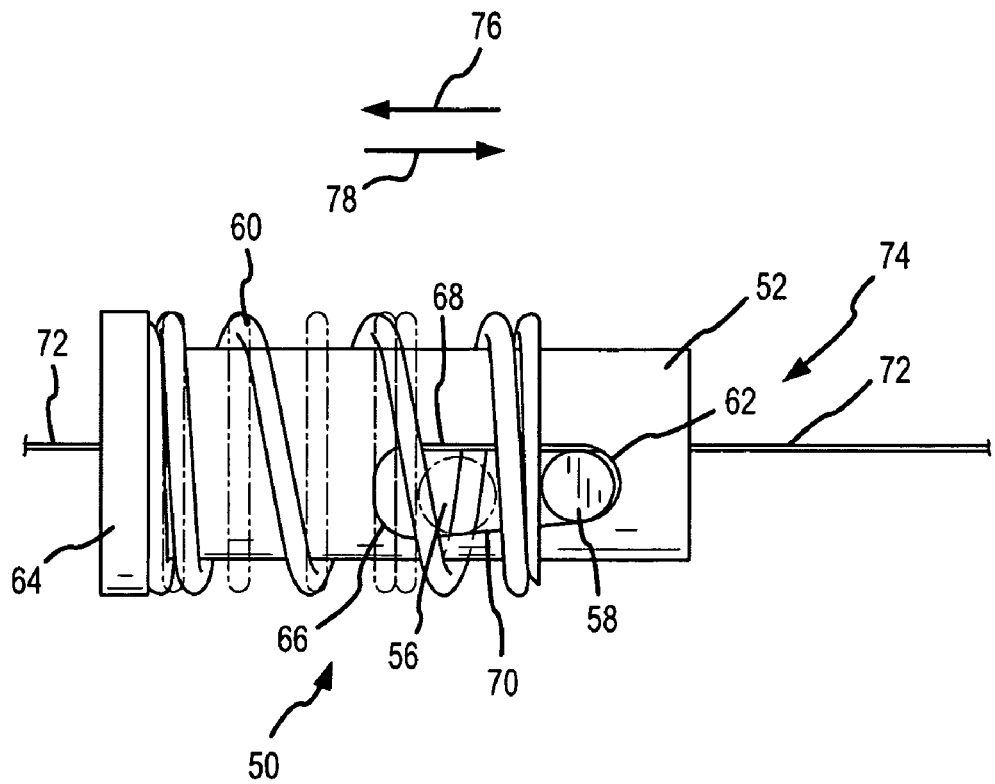
FIG. 6 is a side plan view of the wire lock illustrated in FIG. 5.

Turning now to FIGS. 5 and 6, another embodiment of a wire lock 50 is shown in perspective view and side view, respectively. Wire lock 50 includes a body 52 having an opening 54 extending therethrough, a slot 56 extending across body 52 and intersecting opening 54 at substantially a right angle, and a rigid locking pin 58 disposed within slot 56.

Locking pin 58 permits a wire passing through opening 54 to move freely in a first direction and prevents the wire from moving in a second, opposite direction. To this end, a biasing device 60, such as a spring, biases locking pin 58 towards a locked position against proximal end 62 of slot 56. As shown in FIGS. 5 and 6, biasing device 60 may be a compression member that pushes locking pin 58 against proximal end 62 of slot 56. Biasing device 60 is entrapped between locking pin 58 and a distal end cap 64 of body 52. Though assembly of wire lock 50 is simplified when biasing device 60 is simply entrapped between locking pin 58 and distal end cap 64, biasing device 60 may optionally be attached to either or both of locking pin 58 and distal end cap 64. In addition, a sleeve (not shown) may be placed about all or part of biasing device 60 such that body 52, biasing device 60, and the sleeve are substantially concentrically arranged.

In order to restrain a wire passing through opening 54 in at least one axial direction, one end of slot 56—in particular, proximal end 62 against which biasing device 60 biases locking pin 58—is narrower than a distal end 66 of slot 56. Slot 56 is preferably an elongate slot defined by an axial surface 68, an inclined surface 70 opposite axial surface 68, and proximal and distal ends 62, 66, which join axial surface 68 and inclined surface 70. Inclined surface 70 is inclined relative to a longitudinal axis of body 52 by an angle preferably between about 5 degrees and about 15 degrees, more preferably between about 5 degrees and about 10 degrees, and most preferably about 7 degrees. Locking pin 58 rides on inclined surface 70, while the wire passes and is entrapped between locking pin 58 and axial surface 68. One skilled in the art should thus recognize that adjusting the angle of inclined surface 70 will affect the locking force exerted by locking pin 58 on a wire passing through opening 54.

In use, a flat wire 72 is loaded into wire lock 50 from proximal end 74 (analogous to wire-entry end 26 in FIGS. 1-4) of body 52. To facilitate loading, the operator compresses biasing device 60 into the configuration shown in phantom in FIGS. 5 and 6 by moving locking pin 58 distally. This permits downward movement of locking pin 58 along inclined surface 70, increasing the gap between locking pin 58 and axial surface 68, and thereby permitting wire 72 to pass between locking pin 58 and axial surface 68 and move freely in the direction of arrow 76.

Once locking pin 58 is released, however, biasing device 60 re-expands, its restorative force urging locking pin 58 upwards along inclined surface 70 towards proximal end 62 of slot 56. Wire 72 is now secured between locking pin 58 and axial surface 68. Wire lock 50 is thus self-locking. It should be understood that, depending upon the thickness of wire 72, locking pin 58 may not reach proximal end 62 before wire 72 is suitably entrapped between locking pin 58 and axial surface 68. Further, if one attempts to pull wire 72 in the direction of arrow 78 in an effort to remove it from wire lock 50, the entrapment force exerted on wire 72 will increase as locking pin 58 is forced either against proximal end 62 or into narrower regions of slot 56, again depending upon the thickness of wire 72 and the pulling force exerted, thereby substantially preventing movement of wire 72 in the direction of arrow 78. If one wishes to remove wire 72 from wire lock 50, one pushes locking pin 58 distally (i.e., in the direction of arrow 76), thereby permitting separation between locking pin 58 and axial surface 68 as described above, while simultaneously pulling wire 72 in the direction of arrow 78.

Figure 7:
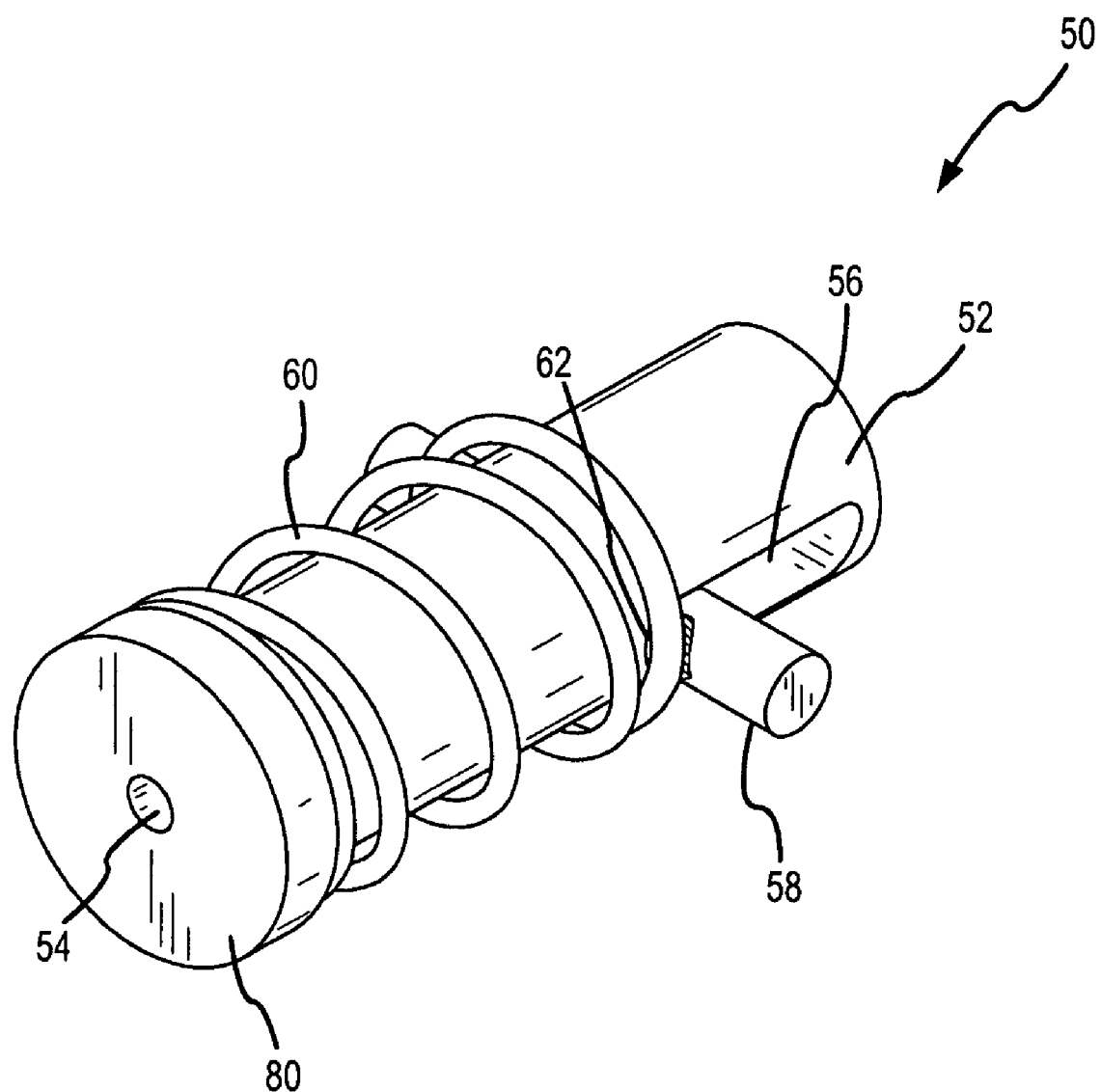
FIG. 7 is a perspective view of a flat wire lock incorporating a tension member biasing device.

Referring now to FIG. 7, a modification to wire lock 50 is shown wherein biasing device 60 is a tension member that pulls locking pin 58 against proximal end 62 of slot 56. So that biasing device 60 may be placed in tension, it is attached to both locking pin 58 and proximal end cap 80, for example by welding, though other methods of attachment are contemplated and regarded as within the scope of the present invention. Operation of the embodiment of wire lock 50 illustrated in FIG. 7 is analogous to the operation of the embodiment of wire lock 50 illustrated in FIGS. 5 and 6, with the principal difference being that, as wire 72 is loaded, biasing device 60 is placed in tension rather than compression by pulling locking pin 58 distally against the restoration force of biasing device 60.

Although four embodiments of this invention have been described above with a certain degree of particularity, those skilled in the art could make numerous alterations to the disclosed embodiments without departing from the spirit or scope of this invention. For example, one or more claw-like locking elements could replace the plurality of locking balls as locking elements 36 in the embodiment illustrated in FIGS. 1-4. Likewise, one or more elastic bands could be used in place of a coil spring for embodiments where loading the wire requires placing the biasing device (18, 60) in tension, and a resilient element could be used in place of a coil spring for embodiments where loading the wire requires placing the biasing device (18, 60) in compression. The device described herein may be incorporated into the handle of a steerable catheter in order to secure the catheter's steering wires therein, though the invention may be practiced with equal benefit in other applications where it is desirable to secure a wire in one direction while permitting free movement of the wire in a second, opposite direction.

All directional references (e.g., upper, lower, upward, downward, left, right, leftward, rightward, top, bottom, above, below, vertical, horizontal, clockwise, and counter-clockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A wire lock, comprising:
a body having an opening extending axially therethrough;
a slot extending across said body, said slot intersecting said opening at substantially a right angle, wherein a distal end of said slot is wider than a proximal end of said slot;
a locking pin disposed within said slot; and
a spring biasing said locking pin towards said proximal end of said slot into a configuration wherein a wire passing through said opening is restrained in at least one axial direction.

2. The wire lock according to claim 1, wherein said slot comprises an elongate slot defined by an axial surface, an inclined surface opposite said axial surface, a distal end surface, and a proximal end surface, said distal and proximal end surfaces joining said axial and inclined surfaces.

3. The wire lock according to claim 2, wherein an angle of said inclined surface relative to a longitudinal axis of said body is between about 5 degrees and about 15 degrees.

4. The wire lock according to claim 3, wherein said angle is between about 5 degrees and about 10 degrees.

5. The wire lock according to claim 4, wherein said angle is about 7 degrees.

6. The wire lock according to claim 2, wherein said locking pin rides on said inclined surface and wherein the wire passes between said locking pin and a surface of said body opposite said inclined surface.

7. A wire lock, comprising:
a body having an opening extending therethrough;
a slot extending across said body and intersecting said opening at substantially a right angle; and
a locking pin disposed within said slot, said locking pin permitting a wire passing through said opening to move freely in a first direction and preventing the wire from moving in a second, opposite direction.

8. The wire lock according to claim 7, wherein said locking pin rides on a first surface partially defining said slot and entraps the wire against a surface of said body opposite said first surface.

9. The wire lock according to claim 8, wherein said first surface is inclined relative to a longitudinal axis of said body at an angle between about 5 degrees and about 15 degrees.

10. The wire lock according to claim 9, wherein said angle is between about 5 degrees and about 10 degrees.

11. The wire lock according to claim 10, wherein said angle is about 7 degrees.

12. The wire lock according to claim 7, further comprising a spring biasing said locking pin towards a locked position.

13. The wire lock according to claim 7, further comprising a biasing device configured to apply pressure between said locking pin and a wire passing through said body.

14. A wire lock, comprising:
a body having an opening extending therethrough;
a slot extending across said body, said slot intersecting said opening at substantially a right angle, said slot including a wide end and a narrow end;
a locking pin disposed within said slot; and
a device biasing said locking pin against said narrow end of said slot such that a wire passing through said opening is permitted to move freely in a first direction and prevented from moving in a second, opposite direction.

15. The wire lock according to claim 14, wherein said biasing device comprises a spring.

16. The wire lock according to claim 14, wherein said biasing device comprises a compression member that pushes said locking pin against said narrow end of said slot.

17. The wire lock according to claim 14, wherein said biasing device comprises a tension member that pulls said locking pin against said narrow end of said slot.

18. The wire lock according to claim 14, wherein a distal end of said slot is wider than a proximal end of said slot.

\* \* \* \* \*